(12) United States Patent
Fletcher

(10) Patent No.: US 6,585,977 B1
(45) Date of Patent: *Jul. 1, 2003

(54) NON-VIRULENT *PORPHYROMONAS GINGIVALIS* MUTANT

(75) Inventor: Hansel M. Fletcher, Loma Linda, CA (US)

(73) Assignee: Loma Linda University, Loma Linda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/762,618

(22) PCT Filed: Aug. 11, 1999

(86) PCT No.: PCT/US99/18197

§ 371 (c)(1),
(2), (4) Date: Feb. 9, 2001

(87) PCT Pub. No.: WO00/09156

PCT Pub. Date: Feb. 24, 2000

Related U.S. Application Data

(63) Continuation of application No. 09/133,089, filed on Aug. 12, 1998, now Pat. No. 6,254,863.

(51) Int. Cl.⁷ ......................... A61K 39/02; A61K 48/00; A61K 39/38; C12N 1/20
(52) U.S. Cl. ................ 424/200.1; 424/93.2; 424/184.1; 424/234.1; 435/252.3; 435/252.1
(58) Field of Search ............................. 424/93.2, 200.1, 424/282.1, 184.1, 234.1; 435/252.1, 252.3

(56) References Cited

U.S. PATENT DOCUMENTS 6,254,863 B1 * 7/2001 Fletcher ...................... 424/93.2

OTHER PUBLICATIONS

Abaibou, H. et al., "A gene in the recA locus affects the virulence potential of *Porphyromonas gingivalis* W83," Abstract 707, Journal of Dental Research, vol. 79, p. 232 (2000.
Abaibou, H. et al., "vim A Gene Downstream of rec A Is Involved in Virulence Modulation in *Porphyromonas gingivalis* W83," Infect. Immun. 69:325–335, Jan. 2001.
Booth, V. et al., "Passive Immunization with Monoclonal Antibodies against *Porphyromonas gingivalis* in Patients with Periodontitis," Infect. Immun. 64:422–427, Feb. 1996.
Chen, T. et al., "*Porphyromonas gingivalis* Gigipains and Adhesion to Epithelial Cells," Infect. Immun. 69:3048–3056, May 2001.
Ebersole, J. L. et al., "Murine Model for Virulence Characteristics of Periodonto–pathogens," Abstract 837, J. Dent. Res. 68:286, 1989.
Fletcher H. M. et al., "Virulence of *Porphyromonas gingivalis* W83 Mutant Defective in the prt H Gene," Infect. Immun. 63:1521–1528, Apr. 1995.

Genco, C. A. et al., "A Peptide Domain on Gingipain R Which Confers Immunity against *Porphyromonas gingivalis* Infection in Mice," Infect. Immun. 66:4108–4114, Sep. 1998.
Gibson, F. C. et al., "Prevention of *Porphyromonas gingivalis*–Induced Oral Bone Loss following Immunization with Gingipain R1,"Infect. Immun. 69P:7959–7963, Dec. 2001.
Kadowaki, T. et al., "Arg–gingipain Acts as a Major Processing Enzyme for Various Cell Surface Proteins in *Porphyromonas gingivalis*," J. Biol. Chem. 273:29072–29076, Oct. 1998.
Kelly, C. G. et al., "The Relationship Between Colonization and Haemagglutination Inhibiting and B Cell Epitopes of *Porhyromonas gingivalis*," Clin. Exp. Immunol. 110:285–291, No. 1997.
Klausen, B. et al., "Periodontal Bone Level and Gingival Proteinase Activity in Gnotobiotic Rats Immunized With *Bacteroides gingivalis*," Oral Microbiol. Immunol. 6:193–201, 1991.
Kuboniwa, M. et al., "Hemoglobin–Binding Protein Purified from *Porphyromonas gingivalis* Is Identical to Lysine–Specific Cysteine Proteinase (Lys–Gingipain)," Biochem. Biophys. Res. Commun. 249:38–43, 1998.
Moritz, A. J. et al., "Immunization With *Porphyromonas gingivalis* Cysteine Protease: Effects on Experimental Gingivitis and Ligature–Induced Periodontitis in *Macaca fascicularis*," J. Periodontol. 69:686–697, 1998.
Nakayama K. et al., "Haemoglobin Receptor Protein is Intragenically encoded by the cysteine Proteinase–Encoding Genes and the Haemagglutinin–encoding gene of *Porphyromonas gingivalis*," Mol. Microbiol. 27:51–61, 1998.
Nakayama, K. et al., "Involvement of Arginine–Specific Cysteine Proteinase (Arg–Gingipain) in Fimbriation of *Porphyromonas gingivalis*," J. Bacteriol. 178:2818–2824, May 1996.

(List continued on next page.)

Primary Examiner—S. Devi
(74) Attorney, Agent, or Firm—David A. Farah; Sheldon & Mak PC

(57) ABSTRACT

A non-virulent, recA defective mutant of *Porphyromonas gingivalis*. The *Porphyromonas gingivalis* strain which is deposited at ATCC under accession number 202109. Also a method of decreasing the growth rate or reproduction rate of *Porphyromonas gingivalis* in a mammal comprising the step of administering to the mammal at least one dose of *Porphyromonas gingivalis* according to the present invention. Further, a method of preventing or treating a *Porphyromonas gingivalis* infection such as periodontitis in a mammal comprising the step of administering to the mammal at least one dose of *Porphyromonas gingivalis* according to the present invention. Further, a method of preventing or treating a *Porphyromonas gingivalis* infection such as periodontitis in a mammal comprising the step of administering to the mammal at least one dose of *Porphyromonas gingivalis* according to the present invention. Also, a pharmaceutical composition comprising a non-virulent, recA defective mutant of *Porphyromonas gingivalis*.

4 Claims, 7 Drawing Sheets

OTHER PUBLICATIONS

O'Brien–Simpson N. M. et al., "Role of RgpA, RgpB, and Kgp Proteinase in Virulence of *Porphyromonas gingivalis* W50 in a Murine Lesion Model," Infection and Immunity 69:7527–7534, Dec. 2001.

Okamoto, K. et al., "Involvement of a Lysine–specific Cysteine Proteinase in Hemoglobin Adsorption and Heme Accumulation by *Porphyromonas gingivalis*," J. Biol. Chem. 273–21225–21231, 1998.

Rajapakse P. S. et al., "Immunization with the RgpA–Kgp Proteinase–Adhesin Complexes of Porphyromonas gingivalis Protects Against Periodontal Bone Loss in the Rat Periodontitis Model," Infect. Immun. 70:2480–2486, May 2002.

Schenkein, H. A. et al., "Increased Opsonization of a prt H–Defective Mutant of *Porphyromonas gingivalis* W83 Is Caused by Reduced Degradation of Complement–Derived Opsonins," J. Immunol. 154–5331–5337, 1995.

Tokuda, M. et al., "Role of *Porphyromonas gingivalis* Protease Activity in colonization of Oral Surfaces," Infect. Immun. 64:4067–4073, Oct. 1996.

Aduse–Opoku, Joseph et al., "Characterization, Genetic Analysis, and Expression of a Protease Antigen (PrpRI) of *Porphyromonas gingivalis* W50," Infection and Immunity 63(12):4744–4754 (1995).

Anderson, D.M. et al., "Functional Properties of Nonhuman Primate Antibody to *Porphyromonas gingivalis*," Infection and Immunity 63(9):3245–3252 (1995).

Barkocy–Gallagher, Genevieve A. et al., "Analysis of the prtP Gene Encoding Porphypain, a Cysteine Proteinase of *Porphyromonas gingivalis*," Journal of Bacteriology 178(10):2734–2741 (1996).

Beck, James et al., "Periodontal Disease and Cardiovascular Disease," J Periodontol 67(10):1123–1137 (1996).

Booth, V. et al., "Passive Immunization with Monoclonal Antibodies against *Porphyromonas gingivalis* in Patients with Periodontitis," Infection and Immunity 64(2):422–427 (1996).

Chen, Priscilla B. et al., "Effect of Immunization on Experimental *Bacteriodes gingivalis*," Infection and Immunity, 55(10):2534–2537 (Oct. 1987).

Christersson, L.A. et al., "Specific Subgingival Bacteria and Diagnosis of Gingivitis and Periodontitis," J Dent Res 68:1633–1639 (1989).

Devereux, John et al., "A comprehensive set of sequence analysis programs for the VAX," Nucleic Acids Research 12(1):387–395 (1984).

Dickinson, Douglas P. et al., "Molecular Cloning and Sequencing of the Gene Encoding the Fimbrial Subunit Protein Protein of *Bacteroides gingivalis*," Journal of Bacteriology 170(4):1658–1665 (1988).

Dusek, David M. et al., "Systemic and Mucosal Immune Responses in Mice Orally Immunized with Avirulent *Salmonella typhimurium* Expressing a Cloned *Porphyromonas gingivalis* Hemagglutinin," Infection and Immunity 62(5):1652–1657 (1994).

Dybvig, Kevin et al., "Degenerate Oligonucleotide Primers for Enzymatic Amplification of recA Sequences from Gram–Positive Bacteria and Mycoplasmas," Journal of Bacteriology 174(8):2729–2732 (1992).

Dzink J.L. et al., "The predominant cultivable microbiota of active and inactive lesions of destructive periodontal diseases," J Clin Periodontal 15:316–323 (1988).

Fletcher, Hansel M. et al., "Virulence of a *Porphyromonas gingivalis* W83 Mutant Defective in the prtH Gene," Infection and Immunity 63(4):1521–1528 (1995).

Fletcher, Hansel M. et al., "Nucleotide Sequence of the *Porphyromonas gingivalis* W83 recA Homolog and Construction of a recA–Deficient Mutant," Infection and Immunity 65(1):4592–4597 (1997).

Fletcher et al, Cloning and sequencing of a recA–like gene from *Porphyromonas gingivalis* W83, J. Dent Res, vol. 76, IADR abstract 1104, p. 151, Nov. 1997.

Fletcher, H.M., Virulence of recA–defective mutants of *Porphyromonas gingivalis* W83, Abstracts of the 97th General Meeting of the American Society for Microbiology, abstract B–424, p. 101, Miami Beach, Florida, May 4–8, 1997.

Genco, C.A. et al. "Characterization of a Tn4351–Generated Hemin Uptake Mutant of *Porphyromonas gingivalis*: Evidence for the Coordinate Regulation of Virulence Factors by Hemin," 63(7):2459–2466 (1995).

Genco, C.A. et al.., "A Peptide Domain on Gingipain R Which Confers Immunity against *Porphyromonas gingivalis* Infection in Mice," Infection and Immunity, 66(9):4108–4114 (Sep. 1998).

Goodman, Heide J.K. et al., "Molecular analysis of the *Bacteriodes fragilis* recA gene," Gene 94:77–82 (1990).

Hamada, Nobushiro et al., "Construction and Characterization of a *fimA* Mutant of *Porphyromonas gingivalis*," Infection and Immunity 62(5):1696–1704 (1994).

Hoover, Charles I. et al., "Transposon–induced pigment–deficient mutants of *Porphyromonas gingivalis*," FEMS Microbiology Letters 124:63–48 (1994).

Houston, Laura et al., "Response of Guinea Pigs to a Vaccine Containing a New Adjuvant (SAF) and Gram–Negative Bacteria," Laboratory Animal Science, 45(1):59–66 (1995).

Kawashima, Hitoshi et al., "Functional Domains of *Escherichia coli* recA Protein Deduced from the Mutational Sites in the Gene," Mol Gen Genet 193:288–292 (1984).

Kesavalu, L. et al., "*Porphyromonas gingivalis* Virulence in Mice: Induction of Immunity to Bacterial Components," Infection and Immunity 60(4):1455–1464 (1992).

Kesavalu, L. et al., "Trypsin–like protease activity of *Porphyromonas gingivalis* as a potential virulence factor in a murine lesion model," Microbial Pathogenesis 20:1–10 (1996).

Kolenbrander, Paul E. et al., "Adhere Today, Here Tomorrow: Oral Bacterial Adherence," Journal of Bacteriology 175(11):3247–3252 (1993).

Kuramitsu, H. et al., "Multiple colonization defects in a cysteine protease mutant of *Porphyromonas gingivalis*," Journal of Periodontal Research 32:140–142 (1997).

Lee, Jin–Yong et al., "*Porphyromonas (Bacteroides) gingivalis* Fimbrillin: Size, Amino–Terminal Sequence, and Antigenic Heterogeneity," Infection and Immunity 59(1):383–389 (1991).

McKee, Ailsa S. et al., "Isolation of colonial variants of *Bacteroides gingivalis* W50 with a reduced virulence," J. Med. Microbiol. 27:59–64 (1988).

Malek, R. et al., "Inactivation of the *Porphyromonas gingivalis fimA* Gene Blocks Periodontal Damage in Gnotobiotic Rats," Journal of Bacteriology 176(4):1052–1059 (1994).

Mayrand, D. et al., "Biology of Asaccharolytic Black–Pigmented Bacteroides Species," Microbiological Reviews 52(1):134–152 (1988).

Moritz, Alan J. et al., "Immunization With *Porphyromonas gingivalis* Cysteine Protease: Effects on Experimental Gingivitis and Ligature–Induced Periodontitis in *Macaca fascicularis*," *J Periodontol* 69(6):686–697 (1998).

Nakayama, Koji et al., "Construction and Characterization of Arginine–specific Cysteine Proteinase (Arg–gingipain)–deficient Mutants of *Porphyromonas gingivalis*," *The Journal of Biological Chemistry* 270(4):23619–23626 (1995).

Nakayama, Koji et al., "Haemoglobin receptor protein is intragenetically encoded by the cysteine proteinase–encoding genes and the haemagglutinin–encoding gene of *Porphyromonas gingivalis*," *Molecular Microbiology* 27(1):51–61 (1998).

Okamoto, Kuniaki et al., "Cloning and Sequencing of the Gene Encoding a Novel Lysine–Specific Cysteine Proteinase (Lys–Gingipain) in *Porphyromonas gingivalis*: Structural Relationship with the Arginine–Specific Cysteine Proteinase (Arg–Gingipain)," *J. Biochem* 120:398–406 (1996).

Park, Yoonsuk et al., "Characterization of the tpr Gene Product and Isolation of a Specific Protease–Deficient Mutant of *Porphyromonas gingivalis* W83," *Infection and Immunity* 61(10):4139–4146 (1993).

Pavloff, Nadine et al., "Molecular Cloning and Characterization of *Porphyromonas gingivalis* Lysin–specific Gingipain," *The Journal of Biological Chemistry* 272(3):1595–1600 (1997).

Pavloff, Nadine et al., "Molecular Cloning and Structural Characterization of the Arg–gingipain Proteinase of *Porphyromonas gingivalis*," *The Journal of Biological Chemistry* 270(3):1007–1010 (1995).

Pearce, B.J. et al., "The rec Locus, a Competence–Induced Operon in *Streptococcus pneumoniae*," *Journal of Bacteriology* 177(1):86–93 (1995).

Rangarajan, Minnie et al., "The prpR1 and prR2 arginine–specific protease genes of *Porphyromonas gingivalis* W50 produce five biochemically distinct enzymes," *Molecular Microbiology* 23(5):955–965 (1997).

Sambrook, J. et al., "Electrophoresis of RNA through Gels Containing Formaldehyde," *Molecular Cloning: A Laboratory Manual* 2:7.43–7.53 (1989).

Schenkein, Harvey A. et al., "Increased Opsonizatin of a prtH–Defective Mutant of *Porphyromonas gingivalis* W83 Is Caused by Reduced Degradation of Complement–Derived Opsonins," *The Journal of Immunology* 5331–5337.

Schenkein, Harvey A., "The effect of periodontal proteolytic *Bacteroides* species on proteins of the human complement system," *Journal of Periodontal Research* 23:187–192 (1988).

Shah, H.N. et al., "Studies on the virulence properties and metabolism of pleiotropic mutants of *Porpyromonas gingivalis* (*Bacteroides gingivalis*) W50," *Oral Microbiol Immunol* 4:19–23 (1989).

Shah, H.N. et al., "Proposal for Reclassification of *Bacteroides asaccharolyticus, Bacteroides gingivalis*, and *Bacteroides endodontalis* in a New Genus, *Porphyromonas*," *International Journal of Systematic Bacteriology* 38(1):128–131 (1988).

Stroeher, Uwe H. et al., "Gene sequence of recA$^+$ and construction of recA mutants of *Vibrio cholerae*," *Mol Gen Genet* 244:295–302 (1994).

Thompson, Stuart A. et al., "Isolation of the *Helicobacter pylori* recA Gene and Involvement of the recA region in Resistance to Low pH," *Infection and Immunity* 63(6):2185–2193 (1995).

Tokuda, Masayuki et al., "Role of Arg–Gingipain A in Virulence of *Porphyromonas gingivalis*," *Infection and Immunity* 66(3):1159–1166 (1998).

Travis, J. et al., "*Porphyromonas gingivalis* proteinases as virulence factors in the development of periodontitis," *Journal of Periodontal Research* 32:120–125 (1997).

van Steenbergen, T.J.M. et al., "Black–Pigmented Oral Anaerobic Rods: Classification and Role in Periodontal Disease," *Periodontal Disease: Pathogens & Host Immune Responses* 41–52 (1991).

Walker, Graham C., "Mutagenesis and Inducible Responses to Deoxyribonucleic Acid Damage in *Escherichia coli*," *Microbiological Reviews* 48:60–93 (1984).

Webster's New World Dictionary, Third College Edition, p. 1419, the definition of "virulence" (1988).

Weinberg, Aaron et al., "Role of Fimbriae in *Porphyromonas gingivalis* Invasion of Gingival Epithelial Cells," *Infection and Immunity* 65(1):313–316 (1997).

Yoneda, M. et al., "Genetic evidence for the relationship of *Porphyromonas gingivalis* cysteine protease and hemagglutinin activities," *Oral Microbiology and Immunology* 11:129–134.

* cited by examiner

NON-VIRULENT *PORPHYROMONAS GINGIVALIS* MUTANT

CROSS-REFERENCE TO RELATED APPLICATION

The present Application is a national phase filing under 35 U.S.C. §371 of PCT Application No. PCT/US99/18197, titled "Non-virulent *Porphyromonas Gingivalis* Mutant" and filed Aug. 11, 1999; which is a continuation of U.S. patent application Ser. No. 09/133,089, titled "Non-Virulent *Porphyromonas Gingivalis* Mutant" and filed Aug. 12, 1998, now U.S. Pat. No. 6,254,863, issued Jul. 3, 2001; the contents of which are incorporated in this disclosure by reference in their entirety.

BACKGROUND

Periodontitis is an inflammatory disease of the tissues surrounding the teeth characterized by loss of the periodontal ligament attachment and alveolar bone support of the tooth. Periodontitis affects more than 49 million people in the United States and hundreds of millions of people worldwide and has been reported as a risk factor for cardiovascular disease and pre-term delivery of low-birth-weight infants. The most common cause of periodontitis is chronic Gram-negative bacterial infections. Among the Gram-negative bacteria implicated as a cause of periodontitis, *Porphyromonas gingivalis* is the major component of the flora in over 90% of adult periodontitis lesions.

Besides being a major etiological agent in adult human periodontitis, *Porphyromonas gingivalis* also causes aspiration pneumonia and necrotizing pneumonia, abscesses in brain, genitourinary tract and lung, as well as mediastinitis. By contrast, *P. gingivalis* is not normally found at healthy sites nor is it found in patients with gingivitis but with no accompanying periodontitis.

The current therapy for periodontitis is directed toward identifying, removing and controlling the etiologic factors, and then correcting the defects these pathogens have caused. These therapies include scaling and root planing, chemotherapy, periodontal surgery and periodic maintenance therapy. However, these treatments are not entirely effective because, for example, the pathogens can become resistant to chemotherapeutic agents.

Several potential virulence factors have been identified which appear to relate to the pathogenicity of *P. gingivalis* in periodontitis. These factors include fimbriae (adhesins), capsule (antiphagocytosis), lipopolysaccharide (bone resorption), proteases (specific and generalized tissue destruction) and a variety of toxic by-products (e.g., ammonia). Some of these factors have been purified and biochemically characterized. However, the specific roles, interactions, relative importance and regulation of these factors remains to be determined.

Therefore, there remains a need for effective prevention and treatment for periodontitis. Further, there remains a need for a modified strain of *P. gingivalis* that can be used as a host genetic background to determine the specific roles, interactions, relative importance and regulation of the potential virulence factors produced by wild-type *P. gingivalis*.

SUMMARY OF THE INVENTION

According to one embodiment of the present invention, there is provided a non-virulent, recA defective mutant of *Porphyromonas gingivalis*. According to another embodiment of the present invention, there is provided a *Porphyromonas gingivalis* strain which is deposited at ATCC under accession number 202109.

According to another embodiment of the present invention, there is provided a pharmaceutical preparation comprising a mutant of *Porphyromonas gingivalis* according to the present invention.

According to another embodiment of the present invention, there is provided a method of decreasing the growth rate or reproduction rate of *Porphyromonas gingivalis* in a mammal, such as a human. The method comprises the step of administering to the mammal at least one dose of a non-virulent, recA defective mutant of *Porphyromonas gingivalis*, such as at least one dose of a *Porphyromonas gingivalis* strain which is deposited at ATCC under accession number 202109.

According to another embodiment of the present invention, there is provided a method of preventing or treating a *Porphyromonas gingivalis* infection such as periodontitis in a mammal, such as a human. The method comprises the step of administering to the mammal at least one dose of *Porphyromonas gingivalis* according to the present invention.

The methods of the present invention can be performed by administering to the mutant with the at least one dose of a non-virulent, recA defective mutant of *Porphyromonas gingivalis* via a route selected from the group consisting of a subcutaneous route, an intravenous route and an intramuscular route, among other routes. In a preferred embodiment, the methods of the present invention include administering at least one dose of a non-virulent, recA defective mutant of *Porphyromonas gingivalis*, wherein the dose is between about a $1 \times 10^3$ and $1 \times 10^7$ bacteria per kg of body weight of the mammal. More preferably, the dose is between about $1 \times 10^5$ and $1 \times 10^6$ bacteria per kg of body weight of the mammal.

BRIEF DESCRIPTION OF THE DRAWINGS

These and other features, aspects and advantages of the present invention will become better understood with regard to the following description, appended claims, and accompanying figures where:

DETAILED DESCRIPTION OF THE INVENTION

Figure 1:
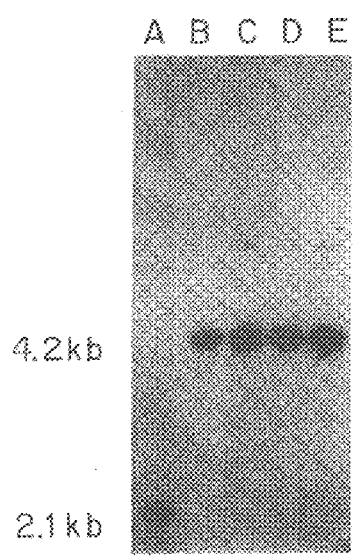
FIGS. 1 and 2 show the results of Southern blot analyses of allelic exchange mutants of *P. gingivalis* to confirm the presence of the ermF-ermAM cassette in a predicted location.

The present invention involves the discovery of a non-virulent mutant of *Porphyromonas gingivalis*. This mutant, designated FLL32, has been found to convey protection against the wild-type *Porphyromonas gingivalis* W83 in mammals when the mammal was immunized with the mutant strain FLL32. Further, FLL32 can be used as a host genetic background to determine the specific roles, interactions, relative importance and regulation of the potential virulence factors produced by wild-type *P. gingivalis*.

All publications mentioned in this document are incorporated by reference in their entirety.

A deposit of *Porphyromonas gingivalis* mutant strain FLL32 has been made at the ATCC, Manassas, Va., US on Apr. 8, 1998, under the accession number 202109. This deposit shall be viably maintained, replacing it if it becomes non-viable, for a period of 30 years from the date of the deposit, or for 5 years from the last date of request for a sample of the deposit, whichever is longer, and made available to the public without restriction in accordance with the provisions of the law. The Commissioner of Patents and Trademarks, upon request, shall have access to the deposit.

In summary, the FLL32 strain was isolated during construction of a mutant recA mutant of *P. gingivalis* W83 wild-type by allelic exchange mutagenesis. The FLL32 strain was recA$^-$ and lacked black pigmentation and β-hemolytic activity on blood agar. Further, the FLL32 strain was deficient in proteolytic activity and significantly more sensitive to UV irradiation than the wild-type W83 strain.

The FLL32 strain exhibited substantially reduced virulence when introduced into mammals and protected those animals immunized with that strain against subsequent infection by the wild-type strain W83. Further, in Western blot experiments of whole cell extracts, unique immunoreactive bands were found in FLL32 using sera from immunized animals. The FLL32 strain is the first nonvirulent recA strain of *P. gingivalis* shown to protect mammals against subsequent infection by the wild-type *P. gingivalis*.

Isolation and Characterization of *P. gingivalis* FLL32 Strain

*Porphyromonas gingivalis* FLL32 was isolated and characterized as follows. First, the recA homolog gene was cloned from wild-type W83. Next, the recA homolog gene was sequenced. Then, an isogenic recA$^-$ mutant of *P. gingivalis* W83 designated FLL32 was constructed by allelic exchange mutagenesis and the presence of the defective recA DNA in the *P. gingivalis* FLL32 strain confirmed by Southern blot analyses.

Next, the phenotype and UV sensitivity of *P. gingivalis* FLL32 strain was determined, as well as its arginine and lysine specific proteolytic activity. Additionally, the amount of its mRNA transcript for the major protease genes was determined. Then, the amount of its C3 complement protein degradation was determined and the amount of C3 accumulation on the surface of the *P. gingivalis* FLL32 strain was determined. Finally, the virulence of the *P. gingivalis* FLL32 strain and protective effect of immunization by the FLL32 strain against subsequent challenge by the wild-type was examined.

(a) Cloning of the recA Homolog Gene from *P. gingivalis* W83

The recA homolog gene was cloned from *P. gingivalis* W83 as follows. First, degenerate oligonucleotide primers (Dybvig, K., et al., "Degenerate oligonucleotide primers for enzymatic amplification of recA sequences from gram-positive bacteria and mycoplasmas." *J. Bacteriol.* 174, 2729–2732, 1992) were used in a polymerase chain reaction (PCR) to amplify a 320 bp fragment of the recA sequence of *P. gingivalis* W83. This PCR fragment was $^{32}$P-labeled and used to screen a λ DASH recombinant phage bank *P. gingivalis* W83 for the presence of hybridizing clones. Ten of 1×10$^3$ phage clone plaques (1.0%) hybridized with the probe.

The hybridizing phage plaques were then amplified and absorbed onto maltose-grown *E. coli* cells. DNA from the phage clones was isolated using the Promega Lambda Wizard DNA Purification system (Promega, Corporation, Madison, Wis.). NotI-BamHI cleavage of purified DNA from two of the recombinants, designated L2 and L10, revealed that the phage clones had different restriction fragment patterns. L2 contained an 8.0 kb and a 6.5 kb fragment that were missing in L10, while L10 contained an 11 kb, a 5.8 kb and a 0.3 kb fragment that were missing in L2. Both L2 and L10 contained a similar 2.1 kb fragment. These data indicated that the L2 and L10 clones were independent clones and not siblings from a single cloning event.

The L10 clone was chosen for further study because it had the smaller fragment insert. Southern blot hybridization using the $^{32}$P-labeled 0.3 kb PCR fragment of the recA gene from the chromosome of W83 was used as a probe to identify the hybridizing fragment. The plasmid pUC19 was used to subclone a 2.1 kb hybridizing BamHI fragment from L10. This clone was designated pFLL26.

(b) Nucleotide Sequencing of the recA Homolog Gene

Both strands of the 2.1 kb hybridizing BamHI fragment from the L10 clone carried on pFLL26 were sequenced and one 1.02 kb open reading frame corresponding to a 36 kDa protein was detected, GenBank Accession Number U70054 (Fletcher et al., 1997). There was a start codon at base position 774. A purine-rich sequence found in *E. coli* ribosome binding sites was also seen three bases upstream from the initiation site. Sequences resembling procaryotic −10 and −35 promoter regions were detected at base positions 749 and 729 respectively. The calculated G+C ratio for the recA homolog gene was 50% which is close to the ratio of 46 to 48% previously reported for genomic *P. gingivalis* DNA (Shah and Collins, 1988).

A comparison of the amino acid sequence of this gene with the National Center for Biotechnology Information genetic sequence databank revealed a similarity of approximately 90, 86 and 82 percent to the RecA proteins from *Bacteroides fragilis*, *Prevotella ruminicola*, GenBank Accession Number U21227, and *Mycobacterium smegmatis*, GenBank Accession Number X99208, respectively. (Goodman and Woods, Molecular Analysis of the *Bacteroides fragilis* recA Gene, Gene 94, pp. 77–82, 1990) Further, regions between amino acids 68 to 81 and 266 to 288 revealed conserved ATP binding domains.

(c) Construction of a recA$^-$Mutant in *P. gingivalis* W83

An isogenic recA$^-$ mutant of *P. gingivalis* W83 was constructed by allelic exchange mutagenesis as follows. The nucleotide sequence of the cloned recA fragment revealed a unique HincII restriction site at bp 435 of the open reading frame (Fletcher, H. M. et al., "Nucleotide sequence of *Porphyromonas gingivalis* W83 recA homolog and construction of a recA-deficient mutant." *Infect.Immun.* 65, 4592–4597, 1997). To utilize this site, a 1.8 kb EcoRI-PstI fragment containing the intact recA gene was subcloned into EcoRI-PstI cleaved pUC19. The resulting plasmid, pFLL23, was digested with HincII and ligated with the 2.1 kb ermF-ermAM cassette from pVA2298 to produce recombinant plasmid designated pFLL24. (See Fletcher, H. M., Schenkein, H. A., Morgan, R. M., Bailey, K. A., Berry, C. R., and Macrina, F. L. (1995). Virulence of a mutant of *Porphyromonas gingivalis* W83 that is defective in the prtH gene. Infect.Immun. 63, 1521–1528).

Then, the recombinant plasmid pFLL24 was used as donor DNA in electroporation of *P. gingivalis* W83. Since the pFLL24 plasmid was unable to replicate in *P. gingivalis*, Clindamycin resistant (Cc$^r$) transformants could only arise as a result of an integration into the wild-type gene on the chromosome. Two double crossover events were predicted between the regions flanking the erm marker and the wild-type recA gene on the chromosome that would result in a replacement of a segment of the wild-type gene with a fragment conferring clindamycin resistance.

Following electroporation and plating on selective medium, 15 Cc$^r$ colonies were detected after a 7 day incubation period. These colonies were replica plated onto selective medium and exposed to UV light to determine their sensitivity. Four UV sensitive colonies, designated FLL32, FLL33, FLL34 and FLL35, were chosen from the unexposed plate for further study.

To confirm the presence of the ermF-ermAM cassette in the predicted location, that is interrupting the recA DNA, Southern blot analyses were performed on the total cellular DNA from *P. gingivalis* wild-type W83, as a control, and from the Cc$^r$ transformants FLL32, FLL33, FLL34 and FLL35. Their DNA was cleaved with BamHI, electrophoresed through 0.7% agarose, bidirectionally transferred to nitrocellulose and probed with $^{32}$P labeled pFLL23 and pVA2198. If the DNA was digested with BamHI, a predicted 2.1 kb fragment would be seen. If the DNA was not digested with BamHI, a predicted 4.2 kb fragment would be seen. Since the ermF-ermAM cassette is missing a BamHI site, any of the four Cc$^r$ transformants with the ermF-ermAM cassette interrupting the recA DNA sequence should have shown a 4.2 kb fragment but not a 2.1 kb fragment.

Figure 2:
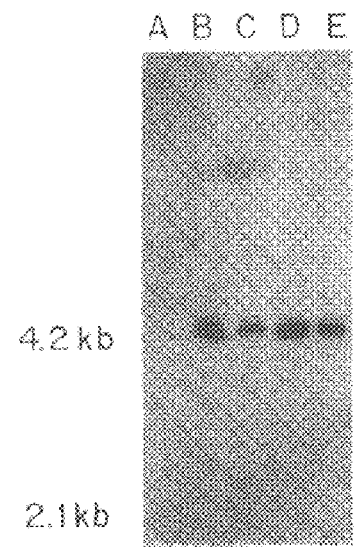

Referring now to FIGS. 1 and 2, there are shown the results of the Southern blot analyses of allelic exchange mutants of *P. gingivalis* to confirm the presence of the ermF-ermAM cassette in the predicted location. As can be seen in FIG. 1, the predicted 2.1 kb fragment was seen in the wild-type *P. gingivalis* W83, lane A, using the $^{32}$P-labeled pFLL23 that carries the *P. gingivalis* recA homolog as a probe, indicated the presence of the recA DNA. In contrast, a 4.2 kb fragment was present in each of the four Cc$^r$ mutants of W83, lanes B-E, FLL32, FLL33, FLL34 and FLL35, respectively, and indicated the presence of the recA DNA sequence interrupted by the ermF-ermAM cassette.

As can be seen in FIG. 2, using pVA2198, which carried the ermF-ermAM cassette as a probe, revealed an identical 4.2 kb hybridizing fragment present in the four Cc$^r$ mutants, lanes B-E, FLL32, FLL33, FLL34 and FLL35, respectively, but not in the wild-type W83, lane A, indicating the presence of the ermF-ermAM cassette only in the transformants. pUC19 vector sequences used as a control did not hybridize with W83 or any of the four Cc$^r$ mutants, FLL32, FLL33, FLL34 and FLL35 (data not shown). These data indicated that recombination had occurred in the four Cc$^r$ mutants, FLL32, FLL33, FLL34 and FLL35, resulting in the wild-type recA gene being interrupted by the ermF-ermAM cassette in FLL32, FLL33, FLL34 and FLL35.

(d) Phenotypic Characterization of *P. gingivalis* W83 recA Mutants

The phenotype of *P. gingivalis* W83 recA mutants were initially characterized as follows. The recA mutants, FLL32, FLL33, FLL34 and FLL35, were plated on Brucella blood agar plates (Anaerobic Systems, Inc., San Jose, Calif.) to determine if any pleotropic effects were associated with inactivation of the recA gene. Two classes of mutants were observed. The first class, a single colony FLL32, was unpigmented and displayed significantly less β-hemolysis than the wild-type W83. The second class contained three strains, FLL33, FLL34 and FLL35, all of which displayed similar P-hemolytic activity and black pigmentation as the wild- type W83. FLL32 and FLL33 were chosen for further study as representatives of their respective classes. A generation time of 3 hours was determined for W83 and of 3.5–4 hours for both FLL32 and FLL33.

(e) Determination of the UV Sensitivity of *P. gingivalis* W83 recA Mutants

To confirm the loss of activity of the *P. gingivalis* RecA protein, the relative sensitivity of the wild-type and recA$^-$ strains to UV irradiation was determined as follows. Wild-type W83 and recA$^-$ mutants FLL32 and FLL33 were exposed to 1000 μjoules of UV irradiation. There was an 80% survival of the wild-type W83 strain in contrast to the 18% survival for FLL32 and FLL33. When wild-type W83 and mutants FLL32 and FLL33 were exposed to 2000 μjoules of UV irradiation, there was 40% survival of the wild-type W83 cells compared to 0% survival for the recA$^-$ mutants FLL32 and FLL33. These data indicated that the recA gene of *P. gingivalis* W83 plays an important role in repairing DNA damage caused by UV irradiation and that both FLL32 and FLL33 were recA defective.

(f) Determination of the Arginine and Lysine Specific Proteolytic Activity of FLL32, FLL33 and W83

The arginine specific proteolytic activity of *P. gingivalis* W83 recA mutants was determined by assaying whole cell preparations from each of the three strains of *P. gingivalis*, FLL32, FLL33 and W83 for proteolytic activity using N-α-benzoyl-DL-arginine p-nitroanilide (BAPNA). Each strain of *P. gingivalis* was grown for 48 hours to late log phase (OD$_{600}$ of 1.2) in 500 ml BHI broth supplemented with hemin and vitamin K. The cells were then washed in PBS (pH 7.3) and resuspended to an OD$_{600}$ of 0.3. 50 μl of the cell samples were incubated for 10 min at 37° C. in 50 mM Tris-HCl (pH 7.0), and 1 mM α-N-benzoyl-arginine-DL-p-nitroanilide (BAPNA) in the presence or absence of 0.5 mM L-cysteine. The control contained buffer alone. Hydrolysis of BAPNA was monitored by the change of absorbance at 410 nm.

Figure 3:
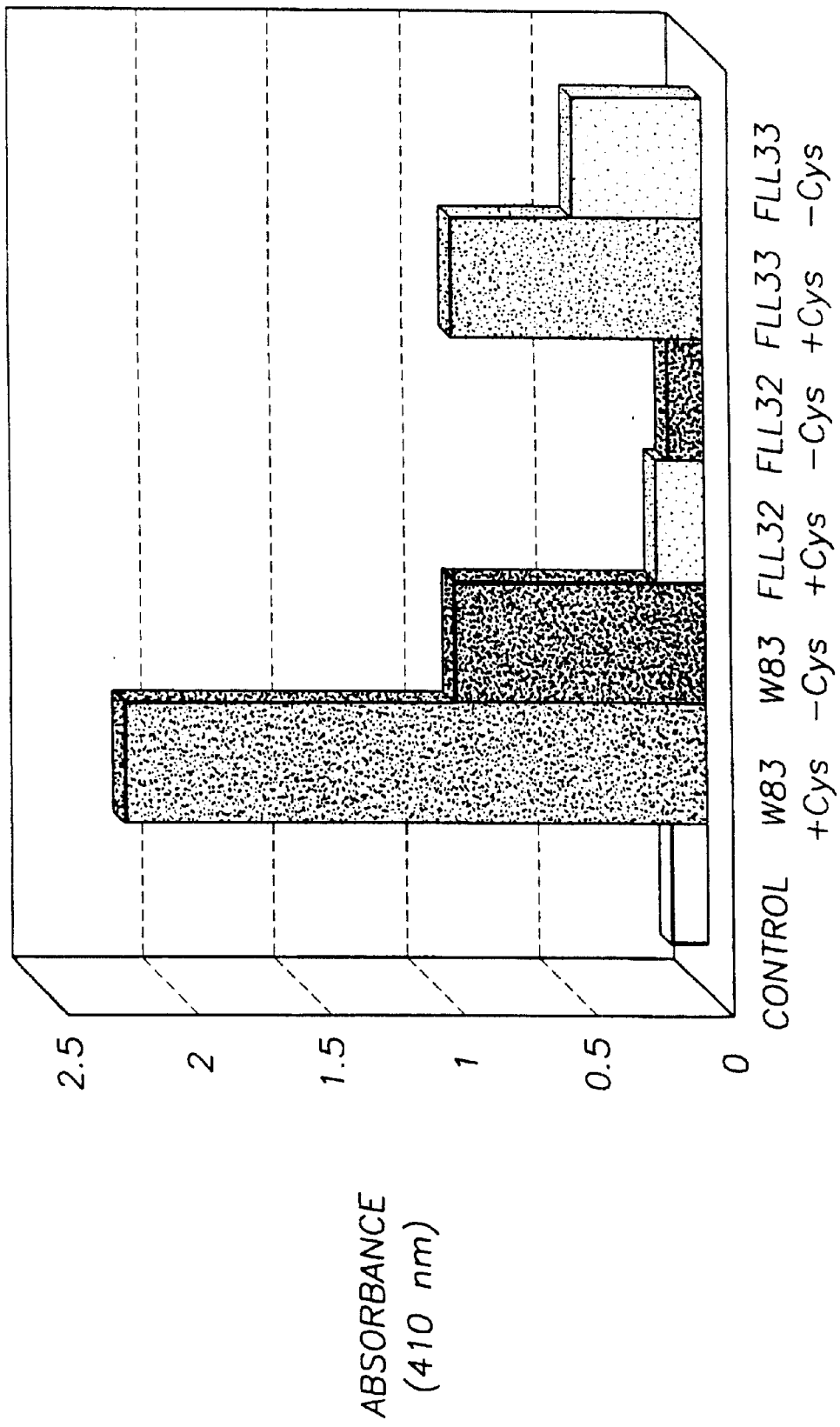
FIG. 3 is a bar graph showing the results of an assay for arginine specific proteolytic activity of *P. gingivalis* FLL32, FLL33 and W83 in the presence or absence of L-cysteine.

Referring now to FIG. 3, there is shown a bar graph of the assay results. As can be seen, the wild-type W83 (–Cys) showed more proteolytic activity than FLL33 (–Cys), while FLL32 (–Cys) did not show significantly more proteolytic activity than the control. The activity from all three strains was enhanced in the presence of cysteine (+Cys) but the relative rates of proteolytic activity remained the same. The reduction of proteolytic activity seen in FLL33 compared to W83 could be related to the longer generation time for the recA$^-$ strains compared to the wild-type W83.

Localization of the arginine-specific proteolytic activity and for lysine-specific proteolytic activity in the recA$^-$ strains was determined as follows. First, extracellular proteolytic activity was tested. Ammonium sulfate was added to 500 ml of culture supernatant from cells grown to late log phase (OD$_{600}$ of 1.2) to 100% saturation. The precipitate was resuspended in 3 ml of PBS (pH 7.3), dialyzed against the same buffer, and then stored at –20° C.

Figure 4:
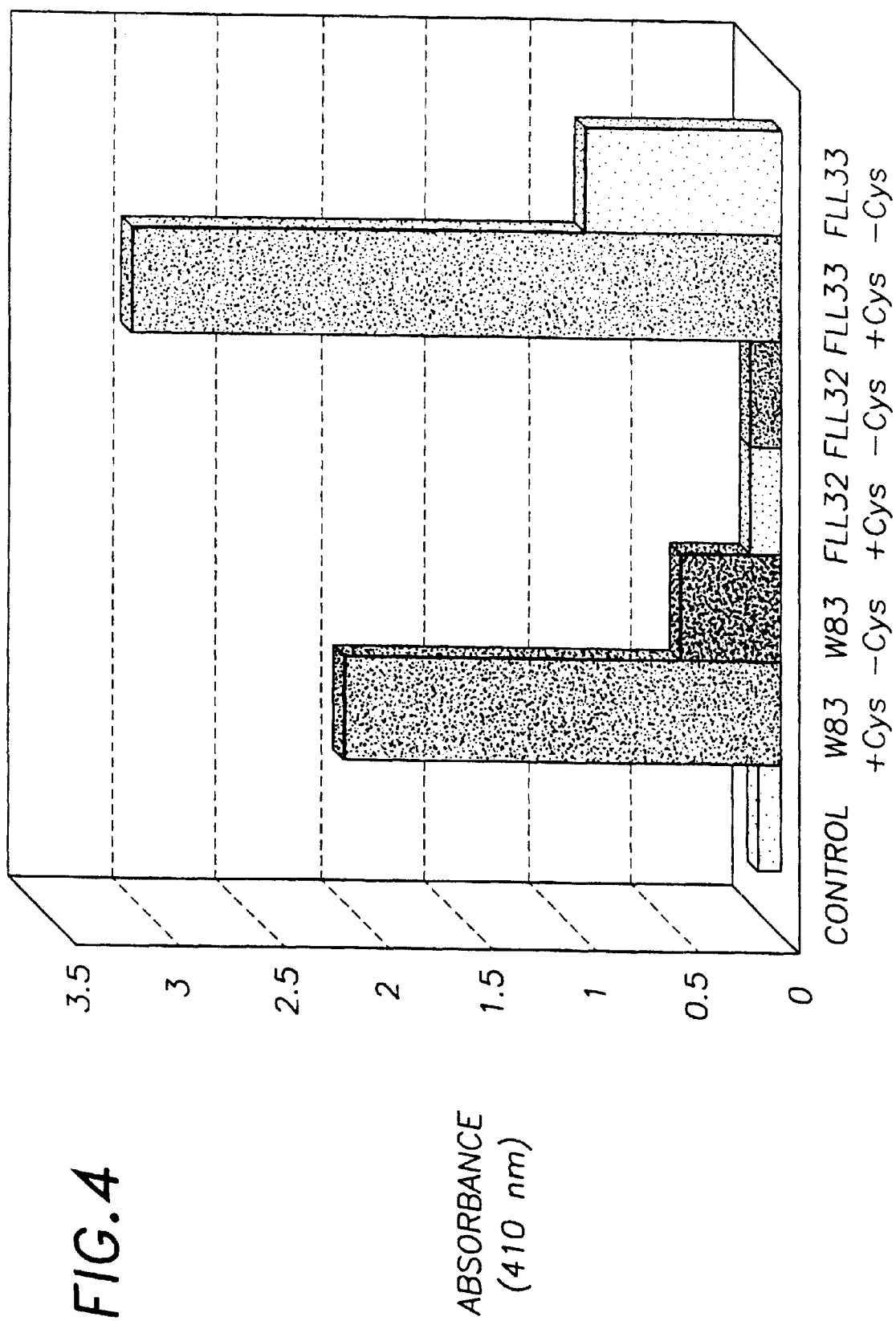
FIGS. 4 and 5 are bar graphs showing the results of an assay for the localization of arginine-specific proteolytic activity and for lysine-specific proteolytic activity, respectively, of *P. gingivalis* FLL32, FLL33 and W83 in the presence or absence of L-cysteine.
Figure 5:
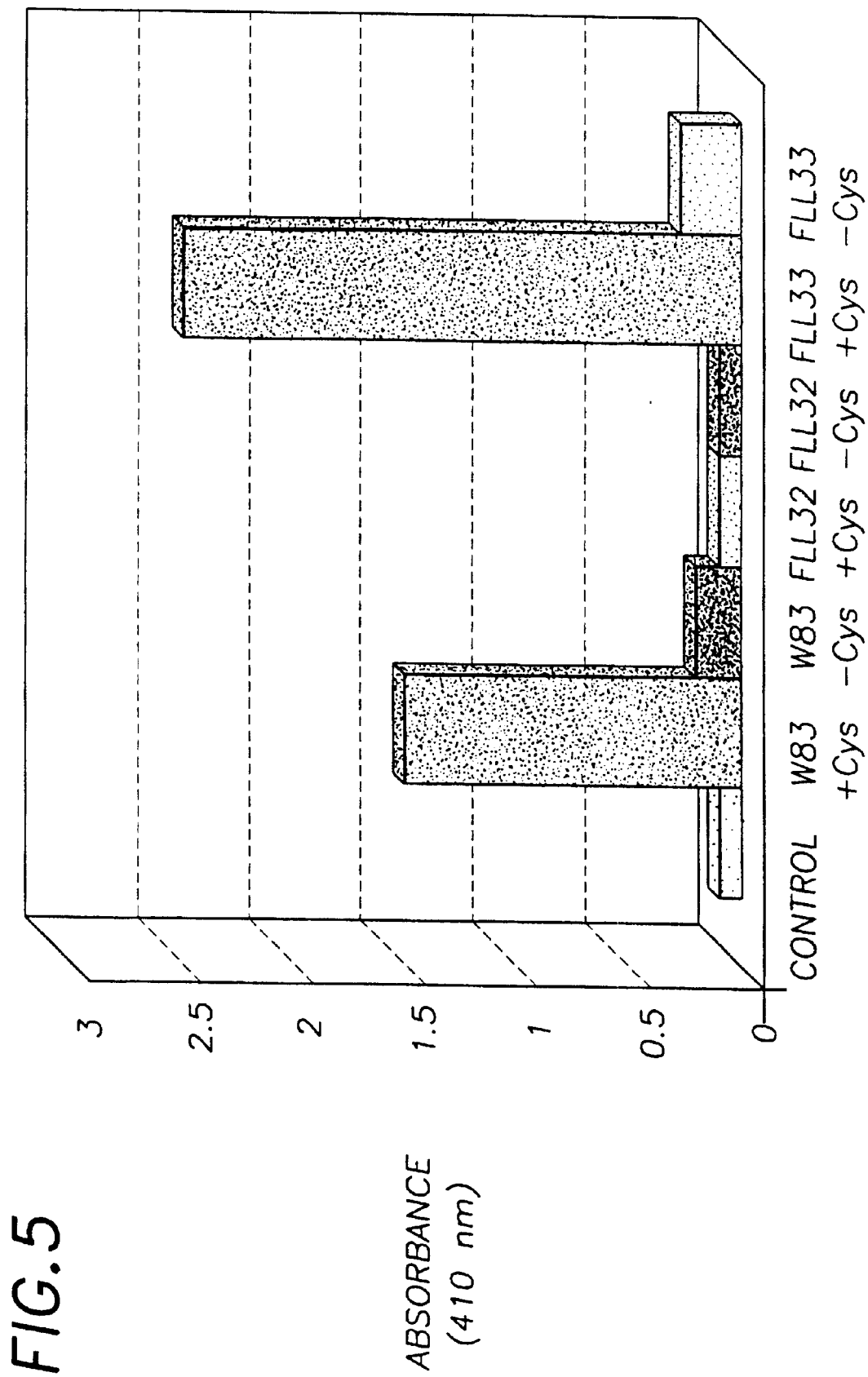

Referring now to FIGS. 4 and 5, there are shown bar graphs showing the results of an assay for the localization of arginine-specific proteolytic activity and for lysine-specific proteolytic activity. As can be seen, the FLL33 showed more extracellular arginine-specific proteolytic activity and more lysine-specific proteolytic activity than the wild-type W83

(−Cys). FLL32 did not show significantly more arginine-specific proteolytic activity or lysine-specific proteolytic activity than the control. Further, the extracellular arginine-specific proteolytic activity of both W83 and FLL33, but not FLL32, was enhanced in the presence of cysteine (+Cys).

Next, intracellular proteolytic activity was tested. The cells from the above experiment were washed in PBS (pH 7.4), and then resuspended in the same buffer to a final volume of 10 ml. 1 ml aliquots were transferred to microcentrifuge tubes containing 0.5 volume of 0.1 mm zirconium beads (Biospec Products, Inc. Bartlesville, Okla.), then lysed in a Mini-Bead Beater homogenizer (Biospec Products) for 3 min. Beads and cellular debris were removed by centrifugation at 12,000×g for 5 min to obtain a clear lysate. Using 100 μg of protein per assay, similar intracellular arginine- and lysine-specific proteolytic activities were observed for the W83 and FLL33 strains, but there was no significant intracellular arginine- or lysine-specific proteolytic activities for FLL32 (data not shown).

(g) Comparison of the Presence and Amount of mRNA Transcript for the Major Protease Genes in FLL32, FLL33 and W83

The loss of proteolytic activity in strain FLL32 could have resulted either from a lack of transcription or translation of the gene, or from a lack of post-translational activation of the precursor product. In order to determine the cause of the loss of proteolytic activity in FLL32, the presence and amount of mRNA transcript for the major protease genes in FLL32, FLL33 and W83 was determined as follows.

First, total RNA was isolated using the Qiagen RNeasy Kit (Qiagen, Valencia, Calif.) from the wild-type W83 strain and from the FLL32 and FLL33 mutants grown to mid-log phase ($OD_{600}$ of 0.2). Unique oligonucleotide primers for prtP (as disclosed in Barkocy-Gallagher, G. A. et al., "Analysis of the prtP gene encoding porphypain, a cysteine proteinase of *Porphyromonas gingivalis*." *J.Bacteriol*. 178, 2734–2741, 1996), prpRI (Aduse Opoku, J. et al., "Characterization, genetic analysis, and expression of a protease antigen (PrpRI) of *Porphyromonas gingivalis* W50." *Infect.Immun*. 63, 4744–4754, 1995) and prtRII were used in RT-PCR to amplify a 1 kb region of the transcripts. Amplified products of the predicted 1 kb size were observed for all three protease gene transcript in all three strains (data not shown). Further, there were no observed differences seen in the concentration of the amplified product between the genes of the three strains. Therefore, both FLL32 and FLL33 strains produce the same mRNA transcripts for the major protease genes in the same amounts as the wild-type W83. As a control, recA intragenic primers amplified the expected 0.72 kb region only in the wild-type W83 strain.

The presence of the mRNA transcripts for the prpRI and prtP proteases in all three *P. gingivalis* strains were further confirmed in Northern blot analysis using an amplified intragenic region of each gene as a probe. Total RNA was extracted from each of the W83, FLL32 and FLL33 strains grown to mid-log phase ($OD_{600}$ of 0.2) using the Qiagen RNeasy midi kit (available from Qiagen, Valencia, Calif., according to the manufacturer's instructions). RNA samples of 1 μg were then separated by agarose gel electrophoresis and transferred to nitrocellulose filter according to the method of Sambrook et al. (Sambrook, J., Fritsch, E. F., and Maniatis, T. (1989). Molecular Cloning: A Laboratory Manual. Second edition. (Cold Spring Harbor, N.Y.: Cold Spring Harbor Laboratory Press)).

Figure 6:
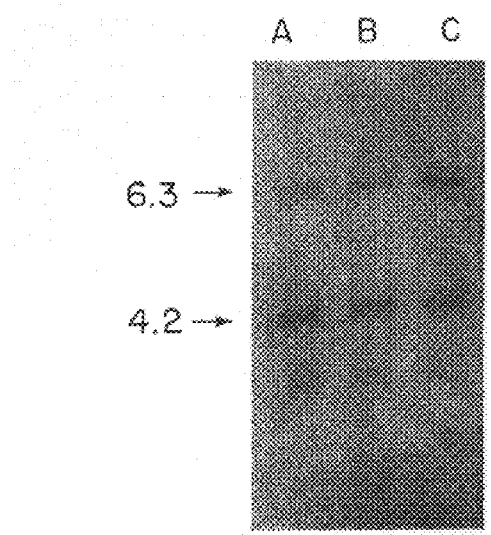
FIGS. 6 and 7 show the results of Northern blot analyses of prpRI and prtP protease genes, respectively, of *P. gingivalis* FLL32, FLL33 and W83.
Figure 7:
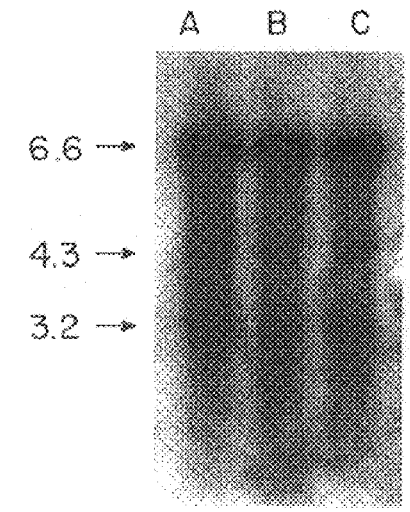

Referring now to FIGS. 6 and 7, there are shown the results of the Northern blot analysis of prpRI and prtP protease genes from the three strains of *P. gingivalis* W83, FLL33 and FLL32. FIG. 6 shows the results using a $^{32}$P-labeled specific intragenic region of prpRI as the probe. FIG. 7 shows the results using a $^{32}$P-labeled specific intragenic region of prpP as the probe. The size of the transcripts in kb are given in the left margins. Lane A shows the results for the W83 wild-type strain, lane B shows the results for the FLL32 mutant strain and lane C shows the results for the FLL33 mutant strain.

As can be seen in FIG. 6, the prpRI probe hybridized to 6.3 and 4.2 kb transcripts. As can be seen in FIG. 7, the prtP probe hybridized to 6.6, 4.3 and 3.2 kb transcripts. The 6.3 and 6.6 kb transcripts for the prpRI and prtP genes, FIGS. 6 and 7 respectively, are consistent with the known size of those genes transcripts. The presence of the smaller transcripts could be degraded product or could be transcripts that share regions of homology with the protease genes. These results confirm the presence of the mRNA transcripts of the prpRI and prtP protease genes in all three strains of *P. gingivalis*, W83, FLL32 and FLL33.

(h) Determination of the C3 Complement Protein Degradation of FLL32, FLL33 and W83

Figure 8:
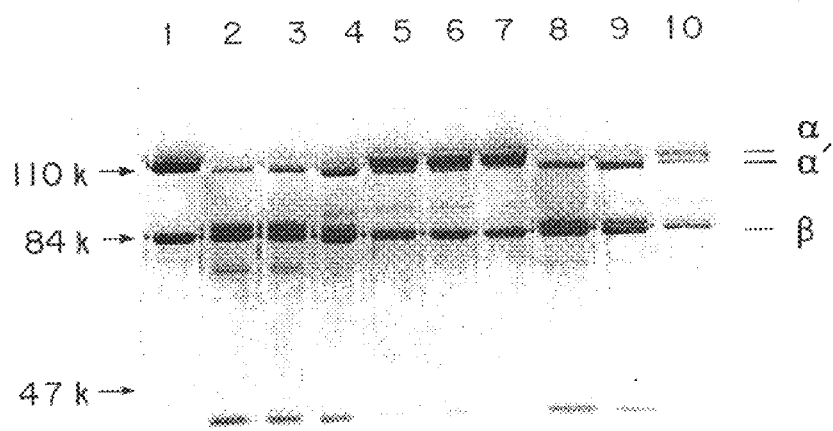
FIG. 8 shows the results of an analysis by SDS-PAGE of the ability of *P. gingivalis* FLL32, FLL33 and W83 to degrade purified C3 complement protein.

The ability of *P. gingivalis* FLL32, FLL33 and W83 to degrade purified C3 complement protein was determined as follows. 1 mg/ml of C3 was incubated with increasing dilutions of each strain at 37° C. for 30 minutes and the supernatant were analysed by SDS-PAGE with 10% separation gels and strained with comassie. The results are shown in FIG. 8 using C3 alone as a control (lane 1), $10^9$ W83 cells/ml (lane 2), $5 \times 10^8$ W83 cells/ml (lane 3), $10^8$ W83 cells/ml (lane 4), $10^9$ FLL32 cells/ml (lane 5), $5 \times 10^8$ FLL32 cells/ml (lane 6), $10^8$ FLL32 cells/ml (lane 7), $10^9$ FLL33 cells/ml (lane 8), $5 \times 10^8$ FLL33 cells/ml (lane 9) and $10^8$ FLL33 cells/ml (lane 10).

As can be seen, the highest concentration of W83 tested (lane 2) completely degraded the α-chain of C3 with generation of C3b and some lower molecular mass fragments similar to C3c and C3d. The lowest bacterial concentration of W83 tested (lane 4) partially degraded the α-chain, causing both α and α'-chains to be visible. Similar results were observed for FLL33 (lanes 8–10). In contrast, the highest concentration of FLL32 (lane 6) only minimally degraded C3 to C3b and lower molecular mass cleavage fragments. There was no degradation of C3 at the lowest bacterial concentration tested for FLL32. Thus, FLL32 is less capable of degrading C3 than either the wild-type W83 or FLL33.

(i) Assessment of C3 Accumulation on FLL32, FLL33 and W83

Figure 9:
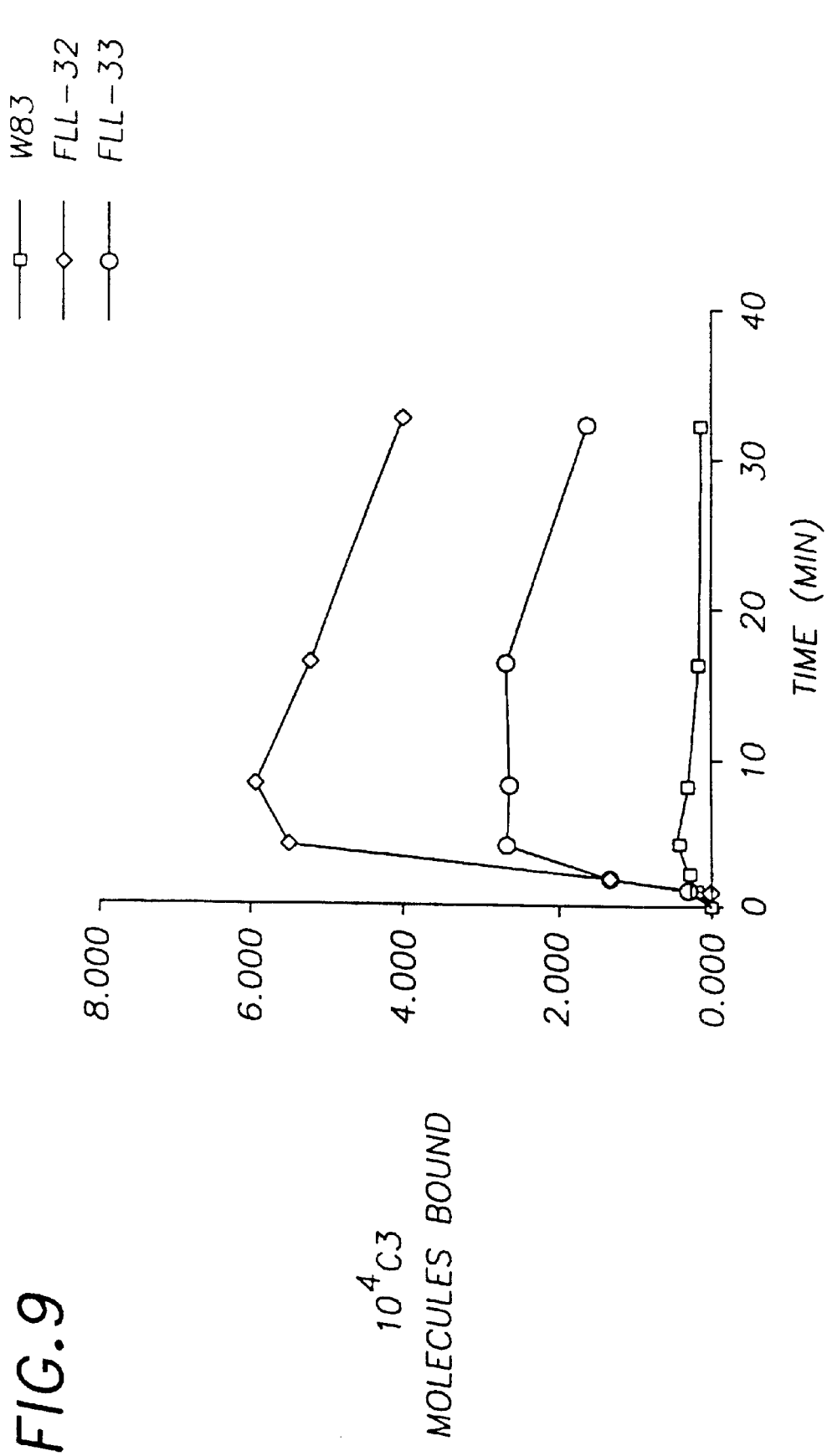
FIG. 9 is a graph showing the results of accumulation of C3 fragments on the bacterial surface of FLL32, FLL33 and W83.

Opsonization of *P. gingivalis* strains W83, FLL32 and FLL33 was assessed for the accumulation of C3 fragments on the bacterial surface as follows. $5 \times 10^8$ cells/ml of each strain was incubated in pooled human serum that was diluted 1:3 with Veronal-buffered saline (0.01 M Veronal buffer, pH 7.5, containing 0.13 M NaCl) and that contained 2 μg/ml $^{125}$I-C3 for 35 minutes. The incubated bacterial samples were then washed and assessed for bound $^{125}$I-C3 fragments by scintillation counting. Referring now to FIG. 9, it can be seen that W83 failed to accumulate substantial amounts of C3 by the end of the incubation period. In contrast, FLL33 accumulated $3 \times 10$ molecules/bacterium and FLL32 accumulated $6 \times 10^4$ molecules/bacterium of $^{125}$I-C3 fragments. Taken together, these results suggest that FLL32 has an increased capacity to be opsonized with C3 fragments compared to both W83 and FLL33.

EXAMPLE I

Comparison of the Virulence Between FLL32, FLL33 and W83 in a Mammal

A first comparison of the virulence between wild-type W83, mutant strain FLL32 and mutant strain FLL33 *Por-* phyromonas gingivalis in a mammal was made as follows. Sixteen female Balb/c mice (8–10 weeks old, Harlan Sprague Dawley Inc., Indianapolis Ind.) were divided into three groups, five in Group I, five in Group II and six in Group III. Each animal received a single challenge dose of $1\times10^{10}$ bacteria P. gingivalis W83 (Group I), FLL33 (Group II) or FLL32 (Group III) by subcutaneous, dorsal surface injection, a dosage of approximately $2\times10^4$ bacterial per kg body weight.

At 24 hours post-challenge, two of the five animals in Group I and one of the five animals in the Group II had died and the remaining animals in both Groups I and II appeared cachectic and hunched with ruffled hair. Although the animals did not display lesions at the dorsal surface site of injection (primary site), all had developed spreading, ulcerative abdominal skin lesions (secondary site). All of the remaining animals in the Group I and three of the four remaining animals in the Group II died by 48 hours post-challenge. The fifth animal in the Group II died by the fourth day post-challenge.

In contrast, all six of the animals in Group III challenged with FLL32 survived the 14 day post-challenge observation period. None of the animals in Group III had any observable negative effects from the challenge.

The data from these challenges were analyzed using Fisher's Exact Test. The analysis found no difference in the virulence between W83 and FLL33 (p=1.000). However, the FLL32 strain had a statistical difference in virulence when compared to FLL33 (p=0.002) and W83 (p=0.002).

A second comparison of the virulence between wild-type W83, mutant strain FLL33 and mutant strain FLL32 Porphyromonas gingivalis in a mammal was made as follows. Seventeen mice Balb/c mice (8–10 weeks old, Harlan Sprague Dawley Inc., Indianapolis Ind.) were divided into three groups, five in Group IV, six in Group V and six in Group VI. Each animal received a single challenge dose of $5\times10^9$ bacteria P. gingivalis W83 (Group IV), FLL33 (Group V) or FLL32 (Group VI) by dorsal subcutaneous surface injection.

At 24 hours post-challenge, one of five animals in Group IV had died and the remaining four had developed ulcerated abdominal skin lesions. By 48 hours post-challenge, three of the remaining animals in Group IV had died. The lesions in the surviving fifth animal were resolving at day 14 post-challenge.

At 24 hours post-challenge, one of six animals in Group V had died and the remaining five had developed ulcerated abdominal lesions. By 48 hours post-challenge, three of the five remaining animals in Group V had died. One additional animal died by day 5 post-challenge. The lesions in the surviving sixth animal were resolving at day 14 post-challenge.

In contrast, all six of the animals in Group VI challenged with FLL32 survived the 14 day post-challenge observation period. None of the animals in Group VI had any observable negative effects from the challenge.

The results of these challenges were analyzed using Fisher's Exact Test. The analysis found no difference in the virulence between W83 and FLL33 (p=0.727). However, the FLL32 strain had a statistical difference in virulence when compared to FLL33 (p=0.008) and W83 (p=0.015).

As can be appreciated from this Example, the inactivation of the recA gene in P. gingivalis FLL33 did not significantly affect the virulence of P. gingivalis. However, the mutation in the FLL32 strain significantly affected the virulence of P. gingivalis.

EXAMPLE II

Demonstration of the Protective Effect of Immunization with FLL32 Against Subsequent Challenge with Wild-Type W83 P. gingivalis The protective effect of immunization of a mammal with FLL32 against subsequent challenge with wild-type W83 P. gingivalis was demonstrated as follows. Sixteen female Balb/c mice (8–10 weeks old, Harlan Sprague Dawley Inc., Indianapolis Ind.) were subcutaneously immunized once per week for 3 weeks with $1\times10^1$ bacteria of the mutant strain FLL32, a dosage of $5\times10^5$ bacteria per kg of body weight. Ten additional female Balb/c mice (8–10 weeks old, Harlan Sprague Dawley Inc., Indianapolis Ind.) were subcutaneously immunized once per week for 3 weeks with sterile phosphate-buffered saline (PBS) as a control. All of the animals immunized with FLL32 and five of the ten animals immunized with PBS were then challenged 2 weeks after the final immunization by subcutaneous injection of a P. gingivalis W83 wild-type suspension containing $1\times10^{10}$ cells, a dosage of $5\times10^5$ bacteria per kg of body weight. The remaining five animals immunized with PBS were challenged 2 weeks after the final immunization by subcutaneous injection of PBS as a control.

By 24 hours post-challenge, one of the five control animals immunized with PBS and challenged with P. gingivalis W83 died and the other four animals had developed spreading infections with secondary site abdominal skin ulcerations and, in some, primary site ulcerations around the base of the tail. All of these mice exhibited severe cachexia with ruffled hair, hunched bodies and weight loss; and all of these five control animals died by four days post-challenge.

In contrast, eight of sixteen animals immunized with P. gingivalis FLL32 and challenged with P. gingivalis W83 displayed only minor secondary skin site abdominal infections by 24 hours post-challenge but all recovered and were alive at the end of the test period. Of the remaining eight animals immunized with P. gingivalis FLL32 and challenged with P. gingivalis W83, five had severe cachexia and died by three days post-challenge, two had moderate cachexia and developed secondary ulcerating abdominal lesions which began to heal at day 5 post-challenge and were alive at the end of the fourteen day experiment period, and the last animal developed a secondary lesion which healed but then developed an additional secondary lesion and died at day 7 post-challenge.

All of the five animals immunized with PBS and challenged with PBS appeared normal throughout the fourteen day experiment period.

The results of these challenges were analyzed using Fisher's Exact Test. The analysis found that immunization with the FLL32 strain protected the animals from a wild-type challenge (p=0.148), while those animals that were immunized with sterile phosphate-buffered saline were not protected (p=0.023).

At the end of the fourteen day experiment period, the ten surviving animals from the group originally immunized with FLL32 and then challenged with W83, and the five animals immunized with PBS and challenged with PBS were sacrificed and their sera were isolated to ascertain the presence of anti-FLL32 antibodies. A 1:1000 dilution of the sera was tested by Western blot analysis for cross-reactivity to whole cell lysates of P. gingivalis W83, FLL32 and FLL33.

Animals immunized with FLL32 were positive for antibodies to each of the P. gingivalis whole cell lysates (data not shown). Immunoreactive bands with molecular mass of 96, 82, 74, 55.2, 49.6, 38, 37, and 35 kDa were observed in the Western blot analyses of each of the whole cell lysates of FLL32, FLL33 and W83. Immunoreactive bands with molecular mass of 44 and 40 kDa were present in the Western blot analyses of each of the whole cell lysates of FLL33 and W83 but were absent from the Western blot analysis of the whole cell lysates of FLL32. Further, immunoreactive bands with molecular mass of 185, 170, 125, 71, 68, 63 and 47 kDa were present in the Western blot analyses of whole cell lysates of FLL32 but were absent in the Western blot analysis of each of the whole cell lysates of FLL33 and the W83 strain.

In contrast, sera from animals immunized with PBS and challenged with PBS were negative for antibodies to each of the *P. gingivalis* whole cell lysates.

EXAMPLE III

Method of Decreasing the Growth Rate or Reproduction Rate Of *Porphyromonas gingivalis* in a Mammal According to one embodiment of the present invention, there is provided a method of decreasing the growth rate or reproduction rate of *Porphyromonas gingivalis* in a mammal, such as a human. The method comprises the step of administering to the mammal at least one dose of a non-virulent, recA⁻ mutant of *Porphyromonas gingivalis*, such as FLL32. The dose can be administered, for example, by subcutaneous, intramuscular or intravenous injection. In a preferred embodiment, the dosage is between about $1\times10^3$ and $1\times10^7$ bacteria per kg of body weight. In a particularly preferred embodiment, the dosage is between about $1\times10^5$ and $1\times10^6$ bacteria per kg of body weight.

Among the uses of decreasing the growth rate or reproduction rate of *Porphyromonas gingivalis* in a mammal, such as a human, is the prevention or treatment of periodontitis, or other diseases or conditions caused in whole or in part by *Porphyromonas gingivalis*, such as aspiration pneumonia and necrotizing pneumonia, abscesses in brain, genitourinary tract and lung, and mediastinitis Although the present invention has been discussed in considerable detail with reference to certain preferred embodiments, other embodiments are possible. Therefore, the spirit and scope of the appended claims should not be limited to the description of preferred embodiments contained herein.

I claim:

1. A method of decreasing the growth rate or reproduction rate of wild-type *Porphyromonas gingivalis* in a mammal, the method comprising administering to the mammal at least one dose of a non-virulent, recA defective mutant of *Porphyromonas gingivalis* which is deposited at ATCC under accession number 202109.

2. The method of claim 1, wherein the mammals a human.

3. The method of claim 1, wherein the administration comprises injecting the mammal with the at least one dose of the non-virulent, recA defective mutant of *Porphyromonas gingivalis* via a route selected from the group consisting of a subcutaneous route, an intravenous route and an intramuscular route.

4. The method of claim 1, wherein the dose administered is between about $1\times10^3$ and $1\times10^7$ the mutant of *Porphyromonas gingivalis* per kg of body weight of the mammal.

* * * * *